United States Patent [19]

Rasmussen et al.

[11] 3,998,958

[45] Dec. 21, 1976

[54] PYRROLIDYLIDENE, PIPERIDYLIDENE AND HEXAHYDROAZEPINYLIDENE UREAS AS CNS DEPRESSANTS

[75] Inventors: Chris Royce Rasmussen, Ambler; Joseph Francis Gardocki, Doylestown; James Nelson Plampin, Roslyn, all of Pa.

[73] Assignee: McNeil Laboratories, Inc., Fort Washington, Pa.

[22] Filed: July 16, 1975

[21] Appl. No.: 600,745

Related U.S. Application Data

[60] Division of Ser. No. 499,706, Aug. 22, 1974, abandoned, which is a continuation-in-part of Ser. No. 335,845, Feb. 26, 1973, abandoned, which is a continuation-in-part of Ser. No. 235,816, March 17, 1972, abandoned.

[52] U.S. Cl. .................. 424/274; 260/239 BF; 424/244; 424/267

[51] Int. Cl.$^2$ ............... A61K 31/33; A61K 31/40; A61K 31/445

[58] Field of Search ............. 260/239 BF; 424/267, 424/244, 274

[56] References Cited

UNITED STATES PATENTS 3,717,648  2/1973  Diana .................. 260/239 BF

*Primary Examiner*—Stanley J. Friedman
*Attorney, Agent, or Firm*—Salvatore R. Conte

[57] ABSTRACT

Compounds of the class of 1-aryl-3-pyrrolidylidene ureas, 1-aryl-3-piperidylidene ureas and 1-aryl-3-hexahydroazepinylidene ureas, useful as central nervous system (CNS) depressants.

7 Claims, No Drawings

PYRROLIDYLIDENE, PIPERIDYLIDENE AND HEXAHYDROAZEPINYLIDENE UREAS AS CNS DEPRESSANTS

CROSS-REFERENCE TO RELATED APPLICATION:

This is a divisional application of my co-pending application Ser. No. 499,706, filed on Aug. 22, 1974, now abandoned, which in turn is a continuation-in-part of application Ser. No. 335,845, filed Feb. 26, 1973, now abandoned, which in turn is a continuation-in-part of application Ser. No. 235,816, filed Mar. 17, 1972, abandoned.

BACKGROUND OF THE INVENTION:

The invention pertains to the field of pyrrolidylidene, piperidylidene and hexahydroazepinylidene ureas which demonstrate CNS depressant activity. In the closest known prior art, Swiss Pat. Appln. No. 11853/68 and U.S. Pat. No. 3,564,010, pyrrolidylidene ureas are disclosed which bear two cyclic substituents in the 3-position of the pyrrolidine ring and in which ring the nitrogen atom is unsubstituted. In contrast, the subject pyrrolidylidene ureas do not have any substituents in the 3-position of the pyrrolidine ring, and, furthermore, the ring nitrogen atom is substituted with either a loweralkyl or benzyl group.

DESCRIPTION OF THE PREFERRED EMBODIMENTS:

The novel pyrrolidylidene, piperidylidene and hexahydroazepinylidene ureas of this invention may be structurally represented by the formula:

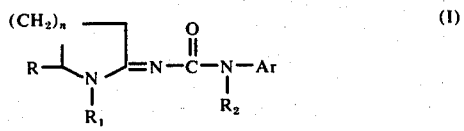

wherein:
  $n$ is the integer 1, 2 or 3;
  R represents a member selected from the group consisting of hydrogen and loweralkyl, preferably methyl;
  $R_1$ represents a member selected from the group consisting of loweralkyl and benzyl;
  $R_2$ represents a member selected from the group consisting of hydrogen and loweralkyl, preferably methyl; and
  Ar represents a member selected from the group consisting of phenyl, naphthyl, mono-, di- and tri-halophenyl, mono-, di- and tri-loweralkylphenyl, mono-, di- and tri-loweralkoxy-phenyl, mono- and di-trifluoromethylphenyl, nitrophenyl, cyanophenyl, methylthiophenyl, loweralkylcarbonyl-phenyl, benzyloxyphenyl, loweralkylhalophenyl, loweralkoxy-halophenyl, benzyloxy-halophenyl, trifluoromethyl-halophenyl and nitro-halophenyl; provided that;
  when said $n$ is 2 or 3, then said R is hydrogen and said $R_1$ is loweralkyl.

The therapeutically active acid addition salts of the foregoing compounds (I) are also included within the scope of this invention.

As used herein, loweralkyl and loweralkoxy may be straight or branch chained and have from 1 to about 5 carbon atoms, such as, for example, methyl, ethyl, propyl, isopropyl, butyl, pentyl and the like alkyls, and, respectively, the corresponding alkoxys such as methoxy, ethoxy, etc. The term halo is generic to bromo, fluoro, iodo and chloro.

The pyrrolidylidene, piperidylidene and hexahydroazepinylidene ureas of formula (I), wherein $R_2$ is hydrogen, are readily obtained by the reaction of an appropriate 2-imino-pyrrolidine, 2-imino-piperidine or 2-imino-hexahydroazepine (II), also known as 2-imino-(tetra-, penta- and hexa-)methylenimines, respectively, with an appropriate phenyl- or naphthylisocyanate (III), preferably employing equimolar amounts in a non-hydroxylic solvent, for example, an aromatic hydrocarbon such as benzene, toluene, xylene and the like, ethers such as dioxane, diethyl ether, tetrahydrofuran and the like, and halogenated hydrocarbons such as methylene chloride, chloroform and the like. In general, no external heating is required to enhance the rate of reaction. The foregoing reaction may be schematically illustrated as follows:

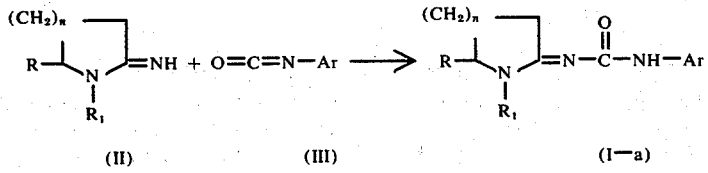

The subject compounds (I), wherein $R_2$ is loweralkyl, may be prepared by the acylation of (II) with an appropriate carbamoyl chloride of formula (IV), preferably employing two molar equivalents of the former to one of the latter. One of the molar equivalents of (II) functions as an HCl scavenger while the other forms the desired urea product. A non-polar solvent is preferably employed, such as previously mentioned, so that the scavenger HCl salt, being insoluble, separates and is easily removed by filtration. The desired urea product (I) which generally stays in solution, is then recovered by conventional techniques, for example, evaporation of the solvent followed by recrystallization workups from conventional solvents. The acylation reaction may be schematically illustrated as follows:

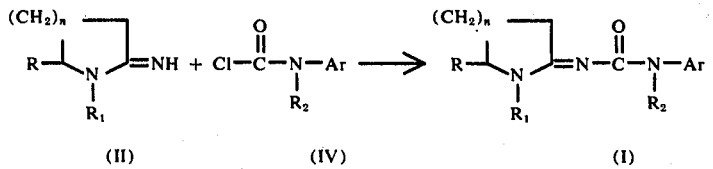

The 2-imino-(tetra-, penta- and hexa-)methylenimines of formula (II) are for the most part described in the literature. To the extent they are not, they are obtained by conversion of the corresponding acid addition salt:

wherein HX represents such typical acids as HCl, HBr, HBF$_4$ and the like. A typical procedure for preparing the salts of formula (V) will be found in Example XLV. The salt-to-base conversion is readily accomplished by treatment with a suitable alkali such as alkali metal or alkaline earth metal hydroxides, carbonates and the like, although a strong alkali such as 10–50% NaOH is preferred in an aprotic solvent such as benzene, ether, and the like. Generally, a minimal amount of water is also employed. The resultant free base (II) remains in solution in the aprotic solvent and the organic solution is used as such in the previously described reaction procedures. Before such use, however, the solution is treated with a drying agent, for example, potassium carbonate, to remove any residual water which could interfere with the subsequent reaction with the isocyanates (III):

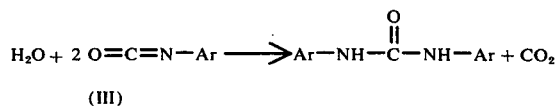

Many of the phenylisocyanates of formula (III) are known, and, to the extent they are not, such may be prepared by methods previously described in the literature, such as, for example, by K. Inukai and Y. Maki, in *Kogyo Kagaku Zasshi*, 67 (5), 807–9 (1964) and in *Kogyo Kagaku Zasshi*, 70 (4), 491–4 (1967), or by J. G. Lombardino and C. F. Gerber in J. Med. Chem., 7, 101 (1964). For example, in accordance with such methods, such phenylisocyanates as the 2,6-di-bromo-(m.p. 68°–70° C.); 3,5-di-chloro- (m.p. 84°–88° C.); 2,6-dimethoxy- (m.p. 32°–35° C.); 3,4-di-methoxy-; 3,4,5-trimethoxy; 3-trifluoromethyl-; and the like derivatives of phenylisocyanates embraced by formula (III) are obtained.

The carbamoyl chlorides of formula (IV) may be prepared by the method of J.A. Aeschlimann described in U.S. Pat. No. 2,449,440. According to this method, an appropriate aniline of the formula:

wherein Ar is as previously described and R$_2$ is loweralkyl, is treated with an excess of Cl$_2$CO to yield the corresponding carbamoyl chlorides of formula (IV):

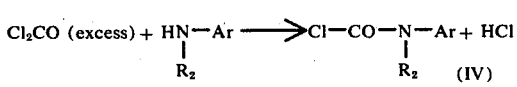

The subject compounds of formula (I) have been found to possess useful pharmacological properties as demonstrated in one or more of the following tests indicative of CNS depressant activity on laboratory animals.

Test A:

An anti-anxiety assay as reported by I. Geller in Phychosomatic Medicine, eds. J. H. Nadine and J. H. Moyer (Lea and Febiger, Phila.) p. 267 (1962) and modified by D. L. Margules and L. Stein in Psychopharmacologia (Berl.) 13, 74–80 (1968). The anti-anxiety activity of the compound to be tested is studied in rats daily for 5 days after i.p. injection of the compound at doses generally ranging from 10–25 mg./kg. body weight and the effect of the compound is observed on the animal's bar pressing rate while working for food reinforcement. The method consists in determining the effect of a test compound on non-punished and punished responses. Hungry rats are trained to press a bar for food reinforcement: a dipper full of milk is delivered to the rat on the average of once every two minutes (variable interval schedule-V.I. II). Following 12 minutes on this schedule, a tone is presented for three minutes which signals the rewarding and simultaneous punishment of each bar press (a dipper full of milk is presented and accompanied by a shock, delivered through the grid floor, with each bar press). The shock delivered is 0.2 milli-seconds in duration and ranges in intensity from 0.5 to 3.5 milli-amperes. Each rat is presented with 4 to 6 alternating pairs of unpunished periods when milk alone is given and punished periods when milk and shock are administered. Control responses are obtained for each rat after saline intraperitoneal injection daily for five days. Each rat is evaluated at the same time of day and in the same test chamber. Responses are recorded and reinforcements (milk) and punishment (shock) delivered by means of suitable automated equipment.

Test B:

A muscle-relaxant assay as judged by the effect of the compound to be tested on strychnine-induced seizures as described by M. J. Orloff et al., Proc. Soc. Exp. Biol. and Med. 70, 254 (1949) as modified by G. Chen and B. Bohner, J. Pharmacol. and Expt. Therap. 117, 142 (1956). The anti-strychnine activity is observed in mice at oral doses of about 25–500 mg./kg. body weight by determining the effect of the compound on the seizure threshold induced by strychnine.

Test C:

An anti-convulsant assay which is a supramaximal electroshock seizure test as described by E. A. Swinyard et al., J. Pharmacol. Expt. Therap. 106, 319 (1952). In this assay, the compound to be tested is administered orally to mice at doses generally ranging from 25–500 mg./kg. body weight and the blocking effect of the compound on the tonic extensor seizure following the application of a supramaximal current to the animal is observed.

Test D:

A mouse behavioral assay as described by S. Irwin, Gordon Research Conference on Medicinal Chemistry, 1959, p. 133. In this assay, such symptoms as ataxia, decrease in motor activity and loss of righting reflex are observed after intraperitoneal (i.p.) administration in mice of the compound to be tested at doses ranging from 10–300 mg./kg. body weight.

In the following table, the CNS profile of several of the subject compounds is listed, as demonstrated by their relative positive responses to one or more of the aforementioned tests. It is understood that the compounds listed therein are not stated for purposes of limiting the invention thereto, but only to show the useful properties of all the compounds within the scope of formula I.

| Compound of Example No. | Active in Test(s) | Compound of Example No. | Active in Test(s) |
| --- | --- | --- | --- |
| I | A | XXVI | B&D |
| II | D | XXVII | B&D |
| III | B&D | XXVIII | C |
| IV | A | XXIX | B&D |
| V | B&D | XXX | B&D |
| VI | A | XXXI | B&D |
| VII | D | XXXII | C |
| VIII | B&D | XXXIII | C |
| IX | A | XXXIV | C |
| X | B&D | XXXV | B&D |
| XI | B&D | XXXVI | B&D |
| XII | C | XXXVII | B&D |
| XIII | C | XXXVIII | A |
| XIV | B&D | XXXIX | C |
| XV | B&D | XL | A |
| XVI | A&C | XLI | A&C |
| XVII | B&D | XLII | C |
| XIX | B&D | XLIII | C |
| XX | B&D | XLIV | B&D |
| XXI | C | XLIX | C |
| XXII | D | L | D |
| XXIII | C | LVIII | C |
| XXIV | A&C | LIX | B&D |
| XXV | C | LXI | B&D |
|  |  | LXIII | B&D |
|  |  | LXVII | C |
|  |  | LXIX | C |

In view of the foregoing, an effective CNS depressant amount of a compound of formula (I) or a therapeutically active acid addition salt thereof intimately admixed with a pharmaceutically acceptable carrier may be systemically administered to warm-blooded animals, including humans, to elicit a CNS depressant response. When administering the hereinabove described dosage unit forms for such purpose, amounts of active ingredient ranging about 15–500 mg, and preferably about 15–250 mg, per dosage unit may be utilized.

For anti-anxiety purposes, the preferred compounds of formula (I) are those wherein Ar is phenyl or a mono-substituted phenyl as previously described. The most preferred compounds are those embraced by the formula:

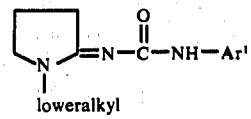

wherein $Ar^1$ is a member selected from the group consisting of halophenyl, loweralkylphenyl, nitrophenyl and trifluoromethylphenyl, and the therapeutically active acid addition salts thereof.

Accordingly, this invention provides a process of alleviating anxiety which comprises systemically administering to an anxious individual, for example, one whose anxiety inhibits his ability to cope with the various requirements of his daily life, or one whose anxiety would have an adverse effect on his physical well-being, an aforementioned compound as the active ingredient in a concentration adequate to elicit an effective anti-anxiety response. Preferably, dosage unit forms containing from about 15 to about 350 mg of such active ingredient are employed for anti-anxiety purposes. A suitable adult human regimen contemplated for the most preferred compounds, 1-(m-chlorophenyl)-3-(1-methyl-2-pyrrolidylidene)urea and 1-(p-nitro-phenyl)-3-(1-methyl-2-pyrrolidylidene)urea, in base or acid addition salt form, is 15–250 mg orally or parenterally administered three or four times a day.

For purposes of relaxing skeletal muscle, the preferred compounds of formula (II) are those wherein Ar is a di-substituted phenyl as previously described. The most preferred compounds are the di-substituted phenyls having the formula:

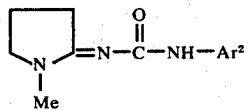

wherein $Ar^2$ is a member selected from the group consisting of dihalophenyl, diloweralkylphenyl and loweralkyl-halophenyl, and the therapeutically active acid addition salts thereof.

Accordingly, this invention provides a process of alleviating muscular pain which comprises systemically administering to a subject with such pain, such as, for example, which may result from muscular spasm or chronic lower back pain, an aforementioned compound as the active ingredient in a concentration adequate to elicit an effective skeletal muscle relaxant response. Preferably, dosage unit forms containing from about 50 to about 400 mg, and, more preferably, from about 125 to 250 mg, of such active ingredient are employed for skeletal muscle relaxant purposes. A suitable adult human regimen contemplated for the most preferred compound, 1-(2,6-dimethylphenyl)-3-(1-methyl-2-pyrrolidylidene)urea, in base or acid addition salt form, is 50–150 mg orally or parenterally administered 4 times a day. Two other preferred compounds, 1-(2,6-dichlorophenyl)-3-(1-methyl-2-pyrrolidylidene)urea and 1-(2-chloro-6-methylphenyl)-3-(1-methyl-2-pyrrolidylidene)urea, in base or acid addition salt form, may be given in dosages of about 125–250 mg four times a day.

To prepare the pharmaceutical compositions of this invention, a compound of formula (I), in base or acid-addition salt form, as the active ingredient is combined in intimate admixture with a pharmaceutically acceptable carrier, which carrier may take a wide variety of forms depending on the form of preparation desired for administration. Either solid or liquid pharmaceutical madia may be employed according to standard pharmaceutical techniques to prepare such typical oral and parenteral formulations as tablets, capsules, powders, suspensions, elixirs, emulsions, solutions, syrups, injectable solutions and suspensions, and the like. Because of their ease in administration, tablets and capsules represent the most advantageous oral dosage form, in which case solid pharmaceutical carriers are obviously employed. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, injections, teaspoonfuls, tablespoonfuls and the like, and segregated multiples thereof.

The following formulations exemplify typical oral and parenteral pharmaceutical compositions in dosage unit form suitable for administration to depressed subjects in accordance with the instant invention.

TABLETS:

The following formulation provides tablets containing 200 mg of 1-(2,6-dimethylphenyl)-3-(1-methyl-2-pyrrolidylidene)urea as the active ingredient (A.I).

|  | mg/tab |
|---|---|
| A.I. | 200.0 |
| Calcium Phosphate, dibasic, N.F. | 120.0 |
| Starch, U.S.P. | 80.0 |
| Starch, U.S.P. (as paste), ca. | 30.78 |
| Magnesium Stearate, U.S.P. | 3.22 |
| Total wt. | 434.0 mg |

Blend the dibasic calcium phosphate, starch and A.I. Mass the above powders with the starch paste. Granulate the mass thru a screen and dry the granulation. Size the granulation while adding the magnesium stearate. Blend the sized granulation and compress the blended granulation into tablet form.

CAPSULES:

The following formulation provides capsules containing 50 mg of 1-m-chlorophenyl-3-(1-methyl-2-pyrrolidylidene)urea as the active ingredient (A.I.).

| McN-3009 Capsule | |
|---|---|
|  | mg/capsule |
| A.I. | 50.0 |
| Lactose, USP | 187.0 |
| Starch, USP | 60.0 |
| Magnesium Stearate, USP | 3.0 |
| Total wt. | 300.0 |

Blend the ingredients thoroughly and fill into suitable two-piece gelatin capsule.

INJECTABLE:

The following formulations provide a lyophilized composition of 1-m-chlorophenyl-3-(1-methyl-2-pyrrolidylidene)urea as the active ingredient (A.I.) which can be reconstituted for parenteral purposes with either of the two indicated vehicles.

| A. Solution for lyophilization: | |
|---|---|
|  | mg/3 ml |
| A.I. | 50.0 |
| Mannitol, USP | 500.0 |
| Water for Injection, USP q.s. ad. (pH adjusted with citric acid) | 3.0 ml |

Add the A.I. to about half of the Water for Injection. Adjust the ph with citric acid until the A.I. is dissolved. Add the mannitol and mix until dissolved. Q.S. to volume the remaining Water for Injection. Filter the solution through a 0.22μ membrane filter and fill into appropriate containers. Lyophilize in an appropriate lyophilizer.

| B. Vehicles for Reconstitution: | Solution No. 1 | Solution No. 2 |
|---|---|---|
|  | mg/ml | mg/ml |
| Citric Acid, USP | 8.4 | 8.4 |
| Sodium Phosphate, N.F. | 5.5 | 5.5 |
| Propylene Glycol, USP | 500.0 | — |
| Alcohol, USP | — | 50.0 |
| Polyethylene Glycol 300, NF | — | 500.0 |
| Preservative | required | required |
| Water for Injection, USP qs. ad. | ml | ml |

Dissolve the citric acid, sodium phosphate and preservative in about half of the Water for Injection. Add the propylene gylcol (Solution No. 1) or polyethylene glycol and alcohol (Solution No. 2) and mix thoroughly. Q.s. to volume with the remaining Water for Injection. Filter through a 0.22μ membrane filter and fill into appropriate containers. Autoclave at 121° C for 20 minutes.

The subject compounds of formula (I), in base form, may be converted to the corresponding pharmaceutically acceptable, therapeutically active, acid addition salt form by reaction with an appropriate inorganic acid, such as, for example, hydrochloric, hydrobromic, hydriodic, sulfuric and the like acids; or with an appropriate organic acid, such as, for example, acetic, propionic, glycolic, lactic, oxalic, malonic, tartaric, citric, sulfamic, ascorbic and the like acids. In turn, the acid addition salt form may be converted to the free base form by conventional treatment with suitable alkali.

Typical examples of the compounds of formula (I), wherein n is 1, R is hydrogen and $R_1$ is methyl, that can be prepared according to the teachings of this invention are the following:

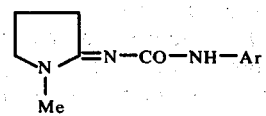

| Ar | Form | Melting Point (°C) |
|---|---|---|
| o-Me-Ph | base | 91–93 |
| m-I-Ph | base | 144–145 |
| 2-Et-6-Me-Ph | $H_2SO_4$ salt | 243–245 |
| o-IsoPr-Ph | HCl salt | 163–165 |
| 4-EtO-Ph | base | 147–148 |

-continued

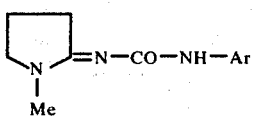

| Ar | Form | Melting Point (° C) |
|---|---|---|
| 2-EtO-Ph | base | 108–110 |
| 4-Cl-2-CF₃Ph | base | 134–135.5 |
| 2,4-di-Cl-Ph | base | 153–155 |
| 5-Cl-2-MeO-Ph | base | 161–163 |

The following examples are intended to illustrate and not to limit the scope of the present invention. Unless otherwise stated, all parts are by weight.

EXAMPLE I 1-(1-Methyl-2-pyrrolidylidene)-3-phenylurea.

After dissolving 4.9 g. (0.05 mole) of 2-imino-1-methylpyrrolidine in anhydrous benzene, 5.96 g. (0.05 mole) of phenylisocyanate is added dropwise with stirring (heat evolves). The reaction mixture is stirred for one-half hour. The solid product which is formed, 1-(1-methyl-2-pyrrolidylidene)-3-phenylurea, is collected (m.p. = 140–144° C.); recrystallized from methanol to give the pure product, m.p. = 146–147.5° C.

EXAMPLE II 1-(1-Methyl-2-pyrrolidylidene)-3-(3,4-dimethoxyphenyl)urea.

After dissolving 5.4 g. (0.055 mole) of 2-imino-1-methylpyrrolidine in dry benzene, 9.85 g. (0.055 mole) of 3,4-dimethoxyphenylisocyanate (prepared according to the method of J. G. Lombardino and C. T. Gerber, J. Med. Chem., 7, Jan. 1964, p. 101), dissolved in dry benzene, is added dropwise to the solution. The reaction mixture is stirred at room temperature overnight (about 16 hrs.). The solvent is evaporated in vacuo and the residue, which solidifies on cooling, is triturated with anhydrous methanol. Repeated recrystallizations from methanol yields the pure product, 1-(1-methyl-2-pyrrolidylidene)-3-(3,4-dimethoxyphenyl)urea, m.p. = 118–120° C.

EXAMPLE III 1-(1-Methyl-2-pyrrolidylidene)-3-p-chlorophenylurea

After dissolving 14.2 g. (0.1445 mole) of 2-imino-1-methylpyrrolidine in anhydrous benzene, 22.2 g. (0.1445 mole) of p- chlorophenylisocyanate dissolved in anhydrous benzene is added slowly with stirring and ice-bath cooling to the above solution. Solid material forms after 10 to 15 mins. The reaction mixture is stirred at room temperature overnight. The solid is collected (m.p. = 138–141° C.) and titurated with hot CH₂Cl₂. The material which does not dissolve is filtered off. Removal of the methylene chloride and recrystallizations from methanol of the subsequent solid product, 1-(1-methyl-2-pyrrolidylidene)-3-p-chlorophenylurea, yields the pure material, m.p. = 142–144° C.

EXAMPLE IV 1-(1-Methyl-2-pyrrolidylidene)-3-p-nitrophenylurea

To a suspension of 6.73 g. (0.05 mole) of 1-methyl-2-iminopyrrolidine hydrochloride in 100 ml. of benzene is added 2 ml. of water followed by 5 ml. of 50% NaOH. After stirring for 5 min., the benzene layer is decanted onto excess anhydrous potassium carbonate. The process is repeated twice with 75 ml. portions of fresh benzene. The combined extracts are filtered rapidly from drying agent (dicalite pad and suction). To the filtrate is added in one portion with stirring 8.21 g. (0.05 mole) of p-nitrophenylisocyanate as a solution in benzene (the isocyanate solution is filtered prior to use). After stirring one hour, the solid, 1-(1-methyl-2-pyrrolidylidene)-3-p-nitrophenylurea, is collected and dried, m.p. = 180°–182° C. Recrystallization from acetone-methanol gives pure product, m.p. = 182°–183° C.

EXAMPLE V 1-(1-Methyl-2-pyrrolidylidene)-3-p-tolylurea

To a suspension of 6.73 g. (0.05 mole) of 1-methyl-2-iminopyrrolidine hydrochloride in 100 ml. of benzene is added 2 ml. of water followed by 5 ml. of 50% NaOH. After stirring for 5 min., the benzene layer is decanted onto anhydrous potassium carbonate. The extraction is repeated twice with 75 ml. portions of fresh benzene. The combined extracts are filtered from drying agent (dicalite pad and suction). To the filtrate is added in one portion with stirring 6.66 g. (0.05 mole) of p-tolylisocyanate. After stirring for 5 hours, the solution is taken to dryness in vacuo and the resulting solid is recrystallized from ethyl acetate to give 1-(1-methyl-2-pyrrolidylidene)-3-p-tolylurea, m.p. = 136°–137° C. A final recrystallization from acetone shows the product melting at 149°–150° C. Thin layer chromatography (TLC) indicates both samples to be identical in purity. Apparently the two melting points represent polymorphic forms.

EXAMPLE VI 1-m-Chlorophenyl-3-(1-methyl-2-pyrrolidylidene)urea

Assuming 100% conversion, 2.94 g. (0.03 mole) of 2-imino-1-methylpyrrolidine is liberated from its HCL salt using the calculated amount of 50% NaOH (2.4 g., 0.03 mole) and extracting into benzene. The benzene solution is dried over K₂CO₃. To this solution, 4.6 g. (0.03 mole) of m-chlorophenylisocyanate dissolved in anhydrous benzene is added dropwise with stirring. Solid forms and the mixture is stirred at room temperature overnight. The solid, 1-m-chlorophenyl-3-(1-methyl-2-pyrrolidylidene)urea, is collected, m.p. = 135°–136° C. A second crop is collected from the mother liquors after taking it to dryness, triturating with hot CHCl₃, and filtering off that which does not dissolve. The two crops are combined and recrystallized from methanol-ether to give the pure product, m.p. = 137°–138° C.

EXAMPLE VII 1-p-Bromophenyl-3-(1-methyl-2-pyrrolidylidene)urea

To 4.9 grams (0.05 mole) of 2-imino-1-methylpyrrolidine in anhydrous benzene is added, dropwise with stirring, 9.9 g. (0.05 mole) of p-bromophenylisocyanate, dissolved in anhydrous benzene. Solid material forms as the reaction mixture is stirred at room temperature overnight. This solid, 1-p-bromophenyl-3-(1-methyl-2-pyrrolidylidene)urea, is collected, (m.p. = 135°–137° C). A second crop (m.p. = 134°–136° C) is also obtained from the mother liquor. The two crops are combined and recrystallized from isopropanol-ether to give pure 1-p-bromophenyl-3-(1-methyl-2-pyrrolidylidene)urea, m.p. = 136°–138° C.

EXAMPLE VIII 1-p-Fluorophenyl-3-(1-methyl-2-pyrrolidylidene)urea

To a solution of 4.9 g. (0.05 mole) of 2-imino-1-methylpyrrolidine in anhydrous benzene is added 6.85 g. (0.05 mole) of p-fluorophenylisocyanate, dissolved in anhydrous benzene, dropwise with stirring. The mixture is stirred at room temperature overnight, then filtered and the filtrate taken to dryness in vacuo. The residue is triturated with isopropanol. The solid which forms is collected, 1-p-fluorophenyl-3-(1-methyl-2-pyrrolidylidene)urea, m.p. = 113°–115° C. Recrystallization from ethyl acetate yields the pure product, m.p. = 115°–116° C.

EXAMPLE IX 1-(1-Methyl-2-pyrrolidylidene)-3-(p-trifluoromethylphenyl)urea

The hydrochloride salt of 2-imino-1-methylpyrrolidine (6.73 g; 0.05 mole) is converted to free base by adding 5 mls. of 50% NaOH and extracting into benzene. After drying over $K_2CO_3$, the benzene layer is stirred at room temperature and 9.36 g. (0.05 mole) of p-trifluorophenylisocyanate [made according to the method of K. Inukai and Y. Maki, Kogyo Kagaku Zasshi, 67 (5) 807–809 (1964)], dissolved in about 50 mls. of anhydrous benzene, is added dropwise to this solution. The reaction mixture is stirred at room temperature for 48 hours and filtered. The filtrate is evaporated to dryness in vacuo and upon triturating with ethyl acetate and cooling, the solid product, 1-(1-methyl-2-pyrrolidylidene)-3-(p-trifluoromethylphenyl)urea, is obtained (m.p. = 128°–131° C.) Recrystallizations from ethyl acetate - petroleum ether affords the pure product, m.p. = 130°–132.5° C.

EXAMPLE X 1-(2,6-Dichlorophenyl)-3-(1-methyl-2-pyrrolidylidene)urea

To a slurry of 6.73 g. (0.05 mole) of 2-imino-1-methylpyrrolidine hydrochloride in 75 ml. of dry benzene is added, with stirring, 2 ml. of water, followed by 6 ml. of 50% NaOH. The benzene is decanted onto anhydrous $K_2CO_3$ and the aqueous layer washed twice with 50 ml. portions of benzene, the benzene being collected by decanting onto the $K_2CO_3$. The benzene extracts are put under nitrogen and dried for 15 minutes, then filtered rapidly through diatomaceous earth (nitrogen blanket) and washed with 100 ml. of benzene. To the filtrate is added 9.4 g. (0.05 mode) of 2,6-dichlorophenylisocyanate, put under nitrogen, stoppered and stirred at room temperature for 2 hours. The mixture is filtered and the solvent removed under reduced pressure. Trituration of the oily residue results in crystallization, 1-(2,6-dichlorophenyl)-3-(1-methyl-2-pyrrolidylidene)urea, and the white crystals are filtered and collected. After recrystallization from benzene-ether-petroleum ether, the m.p. is 134°–136° C.

EXAMPLE XI 1-(4-Chloro-3-trifluoromethylphenyl)-3-(1-methyl-2-pyrrolidylidene)urea The hydrochloride salt of 2-imino-1-methylpyrrolidine (6.73 g; 0.05 mole) is converted to free base by adding 5 ml. of 50% NaOH and extracting into benzene. After drying over $K_2CO_3$, the benzene solution is stirred at room temperature and 11.08 g. (0.05 mole) of 3-trifluoromethyl-4-chlorophenylisocyanate [prepared according to the method of K. Inukai and Y. Maki, Kogyo Kagaku Zasski, 70 (4), 491–4 (1967)] dissolved in about 50 ml. of anhydrous benzene is added dropwise to this solution. After one-half of the amount is added cloudiness occurs and then solid precipitates. The mixture is stirred at room temperature overnight. The solid is collected, 1-(4-chloro-3-trifluoromethylphenyl)-3-(1-methyl-2-pyrrolidylidene)urea, and recrystallizations from ethyl acetate yields the pure product, m.p. = 175° C.

EXAMPLE XII

1-Methyl-3-(1-methyl-2-pyrrolidylidene)-1-phenylurea

The hydrochloride salt of 2-imino-1-methylpyrrolidine (13.46 g.; 0.1 mole) is converted to free base by adding 10 ml. of 50% NaOH and extracting into benzene. After drying over $K_2CO_3$, the benzene layer is stirred at room temperature and 8.48 g. (0.05 mole) of N-methyl-phenylcarbamoyl chloride (prepared according to the method of J. A. Aeschlimann, U.S. Pat. No. 2,449,440), dissolved in anhydrous benzene, is added dropwise to this solution. Cloudiness occurs and then solid precipitates from solution. The mixture is stirred at room temperature overnight and then filtered. The filtrate is taken to dryness in vacuo to an oily residue which is dissolved in hot hexane and filtered hot. Cooling and scratching yields crystals which are collected and recrystallized from hexane to give the pure product, 1-methyl-3-(1-methyl-2-pyrrolidylidene)-1-phenylurea, 27.5°–30° C.

EXAMPLE XIII 1-(3,5-Di-trifluoromethylphenyl)-3-(1-methyl-2-pyrrolidylidene)urea The hydrochloride salt of 2-imino-1-methylpyrrolidine (6.73 g.; 0.05 mole) is converted to free base by adding 5 mls. of 50% NaOH to an aqueous slurry (min. amt. of water added) of the salt and benzene extraction. After drying over $K_2CO_3$, the benzene solution is stirred at room temperature and 12.75 g. (0.05 mole) of freshly distilled 3,5-di-trifluoromethylphenylisocyanate [prepared according to the method of K. Inukai and Y. Maki, Kogyo Kagaku Zasshi, 70 (4), 491–4, (1967)] dissolved in 25 mls. of anhydrous benzene is added dropwise (some heat evolves). The reaction mixture is stirred at room temperature overnight (about 16 hours) and then taken to dryness in vacuo to give a solid residue, 1-(3,5-di-trifluoromethylphenyl)-3-(1-methyl-2-pyrrolidylidene)urea. Recrystallizations from ethyl acetate affords the pure product, m.p. = 165°–166.5° C.

EXAMPLE XIV 1-(2,6-Dimethylphenyl)-3-(1-methyl-2-pyrrolidylidene)urea

To a stirring solution of 6.73 g. (0.05 mole) of 1-methyl-2-iminopyrrolidine hydrochloride in about 2 ml. of water is added about 50 ml. of benzene followed by 10 ml. of 50% NaOH. After stirring 1 min. the benzene layer is decanted onto anhydrous potassium carbonate. The extraction is repeated twice. The combined benzene extracts are filtered from a drying agent (dicalite pad) and rinsed well with dry benzene. To the filtrate is added in one portion with stirring 7.36 g. (0.05 mole) of 2,6-dimethylphenylisocyanate. The reaction mixture is stirred overnight. Solvent removal and recrystallization from ethyl acetate-ether gives the product, 1-(2,6-dimethylphenyl)-3-(1-methyl-2-pyrrolidylidene)urea, as white crystals, m.p. = 119°–120° C.

EXAMPLE XV 1-(2,5-Dichlorophenyl)-3-(1-methyl-2-pyrrolidylidene)urea

To 6.73 g. (0.05 mole) of 1-methyl-2-iminopyrrolidine HCl is added 1 ml. of water and 50 ml. of benzene. After solution is complete (magnetic stirring), 10 ml. of aqueous sodium hydroxide (50%) is added in one portion. After stirring for about 1 min., the benzene layer is decanted onto anhydrous potassium carbonate. The extraction is repeated twice. After drying (occasional swirling) the combined benzene extracts are filtered (dicalite) from drying agent and 9.4 g. (0.05 mole) of 2,5-dichlorophenylisocyanate is added to the filtrate in one portion with swirling. After stirring for 3 hours, the solvent is removed in vacuo affording a colorless solid 1-(2,5-dichlorophenyl)-3-(1-methyl-2-pyrrolidylidene)urea. Recrystallization from acetone (twice) yields the pure product, m.p. = 148.5°–150.5° C.

EXAMPLE XVI 1-m-Methylphenyl-3-(1-methyl-2-pyrrolidylidene)urea

Conversion of the hydrochloride salt of 2-imino-1-methylpyrrolidine (6.73 g.; 0.05 mole) to the free base (4.9 g. assuming 100% conversion) is carried out in the usual manner. After drying over $K_2CO_3$, the benzene layer is stirred, and 6.66 g. (0.05 mole) of m-tolylisocyanate is added (solid forms). The reaction mixture is stirred at room temperature overnight. The solid is collected, m.p. = 148°–149° C. The benzene filtrate, after removal of solvent, yields a further crop of solid material, m.p. 137°–142° C. Recrystallizations of the combined solids from acetone gives the pure product, 1-m-methylphenyl-3-(1-methyl-2-pyrrolidylidene)urea, m.p. = 149°–151° C.

EXAMPLE XVII 1-m-Methoxyphenyl-3-(1-methyl-2-pyrrolidylidene)urea

Conversion of the hydrochloride salt of 2-imino-1-methylpyrrolidine (6.73 g.; 0.05 mole) to the free base (4.9 g. assuming 100% conversion) is carried out in the usual manner. After drying over $K_2CO_3$, the benzene layer is stirred at room temperature and 7.45 g. (0.05 mole) of m-methoxyphenylisocyanate is added. The reaction mixture is stirred overnight and then taken to dryness in vacuo to give a white solid residue of 1-m-methoxyphenyl-3-(1-methyl-2-pyrrolidylidene)urea, m.p. = 123°–125° C. Recrystallizations from acetone affords the pure product, m.p. = 128°–129.5° C.

EXAMPLE XVIII 1-(3,4,5-Trimethoxyphenyl)-3-(1-methyl-2-pyrrolidylidene)urea

The procedure of Example XVII is repeated except that an equivalent amount of 3,4,5-trimethoxyphenylisocyanate is substituted for the m-methoxyphenylisocyanate used therein to yield, as the respective product: 1-(3,4,5-trimethoxyphenyl)-3-(1-methyl-2-pyrrolidylidene)urea.

EXAMPLE XIX 1-(2-Chloro-6-methylphenyl)-3-(1-methyl-2-pyrrolidylidene) urea

Conversion of the hydrochloride salt of 2-imino-1-methylpyrrolidine (6.73 g.; 0.05 mole) to the free base (4.9 g. assuming 100% conversion) is carried out in the usual manner. After drying over $K_2CO_3$, the benzene layer is stirred at room temperature and 8.38 g. (0.05 mole) of 2-chloro-6-methylphenylisocyanate [made according to the method of K. Inukai & Y. Maki, *Kogyo Kagaku Zasshi*, 70 (4) 491–4 (1967)]is added. The reaction mixture is stirred overnight and then taken to dryness in vacuo to give an oil which eventually crystallizes. Recrystallization of the solid, 1-(2-chloro-6-methylphenyl)-3-(1-methyl-2-pyrrolidylidene)urea, from acetone petroleum ether gives the pure product, m.p. = 103°–105.5° C.

EXAMPLE XX 1-(1-Methyl-2-pyrrolidylidene)-3-(m-trifluoromethylphenyl)urea

Conversion of the hydrochloride salt of 2-imino-1-methylpyrrolidine (6.73 g.; 0.05 mole) to the free base (4.9 g. assuming 100% conversion) is carried out in the usual manner. After drying over $K_2CO_3$, the benzene layer is stirred at room temperature and 9.36 g. (0.05 mole) of m-trifluoromethylphenylisocyanate is added (some solid precipitates). The reaction mixture is stirred overnight. The resulting solid is collected, m.p. = 155°–156° C. The benzene filtrate, upon removal of the solvent, affords an additional crop of solid material, m.p. 131°–137° C. Recrystallizations of the combined solids from acetone-pet. ether gives the pure product, 1-(1-methyl-2-pyrrolidylidene)-3-(m-trifluoromethylphenyl)urea, m.p. = 155°–156.5° C.

EXAMPLE XXI 1-(4-Benzyloxyphenyl)-3-(1-methyl-2-pyrrolidylidene)urea

Conversion of the hydrochloride salt of 2-imino-1-methylpyrrolidine (13.46 g.; 0.1 mole) to the free base (9.81 g.; assuming 100% conversion) is carried out in the usual manner. After drying over $K_2CO_3$, the benzene layer is stirred at room temperature and 22.52 g. of p-benzyloxyphenylisocyanate [made according to the method of K. Inukai and Y. Maki, Kogyo Kagaku Zasshi, 70, (4) 491–4 (1967)] dissolved in anhydrous benzene is added. The reaction mixture is stirred overnight and then taken to dryness in vacuo to give a white solid, 1-(4-benzyloxyphenyl)-3-(1-methyl-2-pyrrolidylidene)urea, (m.p. - 138°–140° C.). Recrystallizations from acetone gave the pure product, m.p. = 140°–142° C.

EXAMPLE XXII 1-(1-Methyl-2-pyrrolidylidene)-3-(p-methylthiophenyl)urea

A solution of 1-methyl-2-iminopyrrolidine in benzene is prepared from 6.73 (0.05 mole) of the hydrochloride salt in the following manner. The salt is slurried in 75 ml. of benzene, to which is added 2 ml. of water and 6 ml. of 50% NaOH with vigorous stirring.

The benzene layer is decanted onto anhydrous K₂CO₃ over nitrogen and the aqueous portion washed twice by stirring and decantation with two 50 ml. portions of benzene. The combined benzene extracts are dried over K₂CO₃ under nitrogen with occasional swirling for 15 minutes. The benzene extract is quickly filtered through diatomaceous earth, washed with a 100 ml. portion of dry benzene and transferred, under nitrogen, to a 500 ml. round bottomed flask. To the stirred benzene extract, under nitrogen, there is added 8.25 g. (0.05 mole) of 4-methylthiophenylisocyanate in a small amount of benzene and the reaction is stirred for 3 hours at room temperature. The solvent is removed to dryness under reduced pressure to give a white solid residue, 1-(1-methyl-2-pyrrolidylidene)-3-(p-methylthiophenyl)urea, which is recrystallized from approximately 200 ml. of ethyl acetate to give about 11.25 g. (86% yield) of the product as white needles, m.p. = 141°–144° C.

EXAMPLE XXIII 1-(1-n-Butyl-2pyrrolidylidene)-3-(2,6-dimethylphenyl)urea

The cyclohexylsulfamic acid salt of 1-n-butyl-2-iminopyrrolidine (15.97 g.; 0.05 mole) is converted to free base (7.01 g.; 0.05 mole) in the usual manner. After drying over K₂CO₃, the benzene solution is filtered through diatomaceous earth and 7.36 g. (0.05 mole) of 2,6-dimethylphenylisocyanate is added. The reaction mixture is stirred at room temperature for 3½ hours and then evaporated to dryness in vacuo leaving an oily residue which crystallizes on cooling. Recrystallization from ethylacetate yields the pure product, 1-(1-n-butyl-2-pyrrolidylidene)-3-(2,6-dimethylphenyl)urea, m.p. = 93–95° C.

EXAMPLE XXIV 1-(1-n-Butyl-2-pyrrolidylidene)-3-(m-chlorophenyl)urea

The cyclohexylsulfamic acid salt of 1-n-butyl-2-iminopyrrolidine (15.97 g.; 0.05 mole) is converted to free base (7.01 g.; 0.05 mole) in the usual manner. After drying over K₂CO₃, the benzene solution is filtered through diatomaceous earth and 7.68 g. (0.05 mole) of m-chlorophenylisocyanate is added. The reaction mixture is stirred at room temperature for 2½ hours and then taken to dryness in vacuo leaving a solid residue, 1-(1-n-butyl2-pyrrolidylidene)-3-(m-chlorophenyl)urea. Recrystallizations from ethyl acetate yields the pure product, m.p. = 94–96° C.

EXAMPLE XXV 1-(1-n-Butyl-2-pyrrolidylidene)-3-(2-chloro-5-trifluoromethylphenyl)urea hydrochloride The cyclohexylsulfamic acid salt of 1-n-butyl-2-iminopyrrolidine (7.99 g.; 0.025 mole) is converted to free base (3.5 g.; 0.025 mole) in the usual manner. After drying over K₂CO₃, the benzene solution is filtered through diatomaceous earth and 5.54 g. (0.025 mole) of 2-chloro-5-trifluoromethylphenylisocyanate is added. The reaction mixture is stirred at room temperature for 3 hours and then evaporated to dryness in vacuo leaving an oily residue which crystallizes on cooling, 1-(1-n-butyl-2-pyrrolidylidene)-3-(2-chloro-5-trifluoromethyphenyl)urea, m.p. = 40–45° C. Conversion to the hydrochloride salt yields a white solid, m.p. 178–80° C. Recrystallization from methanol yields the pure HCl salt, m.p. =177–179° C.

EXAMPLE XXVI 1-(1-Methyl-2-pyrrolidylidene)-3-(2,6-diethylphenyl)urea

A solution of 1-methyl-2-iminopyrrolidine in benzene is prepared from 13.46 g. (0.1 mole) of the hydrochloride salt in the usual manner. 2,6-Diethylphenylisocyanate (b.p. 103–105° C. at 1.0 mm. Hg) is prepared (in 89% yield) from 2,6-diethylaniline according to the method of K. Inukai and Y. Maki, *Kogyo Kagaku Zasshi*, 70, (4) 491–4 (1967) and a benzene solution of 17.5 g. (0.1 mole) is added to the former benzene solution. The reaction becomes warm and is stirred for 2 hours. The solvent is removed under reduced pressure to yield a pale yellow oily residue which readily crystallizes when treated with ether-pet. ether to give white crystals of 1-(1-methyl-2-pyrrolidylidene)- 3-(2,6-diethylphenyl)urea. After recrystallization from ether, the m.p. is 71°–73° C.

EXAMPLE XXVII 1-(1-Methyl-2-pyrrolidylidene)-3-(2,6-dibromophenyl)urea

A solution of 1-methyl-2-iminopyrrolidine in benzene is prepared from 6.73 g. (0.05 mole) of the hydrochloride salt in the usual manner. 2,6-Dibromophenylisocyanate (m.p. 68°–70° C.) is prepared (in 70% yield) from 2,6-dibromoaniline according to the method K. Inukai and Y. Maki, *Kogyo Kagaku Zasshi*, 70, (4) 491–4 (1967) and a benzene solution of 13.85 g. (0.05 mole) is added to the former benzene solution. The reaction mixture is stirred for 3½ hours. The solvent is removed under reduced pressure to give a pale yellow solid residue which is recrystallized twice from ethyl acetate to give the product, 1-(1-methyl-2-pyrrolidylidene)-3-(2,6-dibromophenyl)urea, as pale yellow crystals, m.p. =115°–117° C.

EXAMPLE XXVIII 1-(1-Methyl-2-pyrrolidylidene)-3-(2,6-dimethoxyphenyl)urea

A solution of 1-methyl-2-iminopyrrolidine in benzene is prepared from 10.73 g. (0.08 mole) of the hydrochloride salt in the usual manner. 2,6-Dimethoxyphenylisocyanate is prepared in 81% yield (crude) from 2,6dimethoxybenzoyl chloride by the method of K. Inukai and Y. Maki, *Kogyo Kagaku Zasshi*, 67, (5) 807–9 (1964). A benzene solution of 13.45 g. (0.075 mole) of the 2,6-dimethoxyphenylisocyanate is added to the benzene solution of 1-methyl-2-iminopyrrolidine and the reaction mixture is stirred for 1.5 hours at room temperature. A white precipitate, which forms, is filtered off and discarded. The filtrate is reduced to dryness reduced pressure to give a clear, viscous oil that crystallizes on cooling. Recrystallizations from ethyl acetate-ether and ethyl acetate gives 1-(1-methyl-2-pyrrolidylidene)-3-(2,6-dimethoxyphenyl)urea as white crystals, m.p. = 114°–117° C.

EXAMPLE XXIX 1-(1-Benzyl-2-pyrrolidylidene)-3-(m-chlorophenyl)urea

The fluoroborate salt of 1-benzyl-2-iminopyrrolidine (6.55 g.; 0.025 mole) is converted to free base (4.36 g.;

0.025 mole — assuming 100% conversion) by adding 5 ml. of 50% NaOH to an aqueous slurry of the salt and benzene extraction. After drying over $K_2CO_3$, the benzene solution is filtered through diatomaceous earth and 3.84 g. (0.025 mole) of m-chlorophenylisocyanate, dissolved in anhydrous benzene, is added. The reaction mixture is stirred at room temperature for 2 hours and then taken to dryness in vacuo to give an oily residue which eventually crystallizes. Recrystallizations from acetonepetroleum ether affords a pure product, 1-(1-benzyl-2-pyrrolidylidene)-3-(m-chlorophenyl)urea, m.p. = 91°–93° C.

EXAMPLE XXX 1-(1-Benzyl-2-pyrrolidylidene)-3-(3-chloro-4-fluorophenyl)urea

The fluoroborate salt of 1-benzyl-2-iminopyrrolidine (6.55 g.; 0.025 mole) is converted to the free base (4.36 g.; 0.025 mole) in the usual manner. After drying over $K_2CO_3$, the benzene solution is filtered through diatomaceous earth and 4.29 g. (0.025 mole) of 3-chloro-4-fluorophenyl-isocyanate is added. The reaction mixture is stirred at room temperature for 1 hour and then evaporated to dryness in vacuo to give a solid residue. Recrystallizations from acetone-ether yields the pure product, 1-(1-benzyl-2-pyrrolidylidene)- 3-(3-chloro-4-fluorophenyl)urea, m.p. = 131°–132° C.

EXAMPLE XXXI 1-(1-Benzyl-2-pyrrolidylidene)-3-(4-methylthiophenyl)urea

The fluoroborate salt of 1-benzyl-2-iminopyrrolidine (6.55 g.; 0.025 mole) is converted to the free base (4.36 g.; 0.025 mole) in the usual manner. After drying over $K_2CO_3$, the benzene solution is filtered through diatomaceous earth and 4.13 g. (0.025 mole) of 4-methylthiophenylisocyanate is added. The reaction mixture is stirred at room temperature for 1 hour and then evaporated to dryness in vacuo to give an oil which crystallizes. Recrystallizations from acetone-ether yields the pure product, 1-(1-benzyl-2-pyrrolidylidene)-3-(4-methylthiophenyl)urea, m.p. = 113°–115° C.

EXAMPLE XXXII 1-(1-Benzyl-2-pyrrolidylidene)-3-(m-trifluoromethylphenyl)urea hydrochloride The fluoroborate salt of 1-benzyl-2-iminopyrrolidine (6.55 g.; 0.025 mole) is converted to free base (4.36 g.; 0.025 mole) in the usual manner. After drying over $K_2CO_3$, the benzene solution is filtered through diatomaceous earth and 4.68 g. (0.025 mole) of m-trifluoromethylphenylisocyanate is added. The reaction mixture is stirred at room temperature for 1 hour and then evaporated to dryness in vacuo to give an oily residue of 1-(1-benzyl-2-pyrrolidylidene)-3-(m-trifluoromethylphenyl)urea which is dissolved in ether and converted to the hydrochloride salt. Recrystallizations from acetone-ether yields the pure product, 1-(1-benzyl-2-pyrrolidylidene)-3-(m-trifluoromethylphenyl)urea HCl, m.p. = 164°–165° C.

EXAMPLE XXXIII 1-(1-Benzyl-2-pyrrolidylidene)-3-(2,6-dimethylphenyl)urea HCL The fluoroborate salt of 1-benzyl-2-iminopyrrolidine (6.55 g.; 0.025 mole) is converted to free base (4.36 g.; 0.025 mole) in the usual manner. After drying over $K_2CO_3$, the benzene solution is filtered through diatomaceous earth and 3.68 g. (0.025 mole) of 2,6-dimethylphenylisocyanate is added. The reaction mixture is stirred at room temperature for 1 hour and then evaporated to dryness in vacuo to give an oily residue of 1-(1-benzyl-2-pyrrolidylidene)-3-(2,6-dimethylphenyl)urea which is dissolved in ether and converted to the hydrochloride salt. Recrystallizations from methanol yields the product, 1-(1-benzyl-2-pyrrolidylidene)-3-(2,6-dimethylphenyl)urea HCl, m.p. = 185°–195° C. (dec.)

EXAMPLE XXXIV 1-(1-n-Butyl-2-pyrrolidylidene)-3-(3-chloro-2-methylphenyl)urea hydrochloride hydrate The cyclohexylsulfamic acid salt of 1-n-butyl-2-iminopyrrolidine (7.99 g.; 0.025 mole) is converted to free base (3.5 g.; 0.025 mole) by adding 2.5 ml. of 50% NaOH to an aqueous slurry of the salt and benzene extraction. After drying over $K_2CO_3$, the benzene solution is filtered through diatomaceous earth and 4.19 g. (0.025 mole) of 3-chloro-2-methylphenylisocyanate is added. The reaction mixture is stirred at room temperature for 3 hours and then taken to dryness in vacuo to give an oily residue of 1-(1-n-butyl-2-pyrrolidylidene)-3-(3-chloro-2-methyl-phenyl)urea which is dissolved in ether and converted to the hydrochloride salt. Recrystallization from methanol-ether yields the product, 1-(1-n-butyl-2-pyrrolidylidene)-3-(3-chloro-2-methylphenyl)urea HCl hydrate, m.p. = 126°–128° C.

EXAMPLE XXXV 1-(3,5-Dichlorophenyl)-3-(1-methyl-2-pyrrolidylidene)urea

The hydrochloride salt of 2-imino-1-methylpyrrolidine (13.46 g.; 0.1 mole) is converted to free base by adding 10 ml. of 50% NaOH and extracting into benzene. After drying over $K_2CO_3$, the benzene solution is filtered through diatomaceous earth and 18 g. of 3,5-dichlorophenylisocyanate [made according to the method of K. Inukai and Y. Maki, *Kogyo Kagaku Zasshi* 70 (4), 491–4 (1967)] dissolved in dry benzene, is added and the reaction mixture quickly stoppered. The reaction mixture is stirred at room temperature for 80 minutes and then filtered. The filtrate is taken to dryness in vacuo to give a red-brown oily residue which is dissolved in hot EtOAc and treated with charcoal. The filtrate is reduced in volume and cooled to produce crystals of 1-(3,5-dichlorophenyl)-3-(1-methyl-2-pyrrolidylidene)urea. REcrystallizations from ethyl acetate yields the pure product, m.p. = 157°–159° C.

EXAMPLE XXXVI 1-(1-Methyl-2-pyrrolidylidene)-3-(2,4,6-tribromophenyl)urea

The hydrochloride salt of 2-imino-1-methylpyrrolidine (6.73 g.; 0.05 mole) is converted to free base (4.0 g.; 0.05 mole — assuming 100% conversion) by adding 5 ml. of 50% NaOH to an aqueous slurry (minimal amount of water) of the salt and benzene extraction. After drying over K₂CO₃, the benzene solution is stirred at room temperature and 16.79 g. (0.0472 mole) of 2,4,6-tribromophenylisocyanate [made according to the method of K. Inukai and Y. Maki, *Kogyo Kagaku Zasshi*, 70 (4), 491–4 (1967)] dissolved in anhydrous benzene, is added with stirrng. The reaction mixture is stirred for 2 hours and then the solvent is evaporated in vacuo to give a solid residue of 1-(1-methyl-2-pyrrolidylidene)-3-(2,4,6-tribromophenyl)urea. Recrystallizations from acetone yields the pure product, m.p. = 165°–167.5° C.

EXAMPLE XXXVII 1-(2,4,6-Trichlorophenyl)-3-(1-methyl-2-pyrrolidylidene)urea

The hydrochloride salt of 2-imino-1-methylpyrrolidine (5.52 g., 0.041 mole) is converted to free base in benzene in the usual manner. Then 9.08 g. (0.041 mole) of 2,4,6-trichlorophenylisocyanate [made according to the method of K. Inukai and Y. Maki, *Kogyo Kagaku Zasshi*, 70 (4), 491–4 (1967)] dissolved in anhydrous benzene is added with stirring. The reaction mixture is stirred for 2 hours and the solvent is evaporated in vacuo to give a solid residue of 1-(2,4,6-trichlorophenyl)-3-(1-methyl-2-pyrrolidylidene)urea. Recrystallizations from ethyl acetate yields the pure product, m.p. = 160°–162° C.

EXAMPLE XXXVIII 1-(3-Bromophenyl)-3-(1-methyl-2-pyrrolidylidene)urea

The hydrochloride salt of 2-imino-1-methylpyrrolidine is converted to the free base (4.9 g.; 0.05 mole) in benzene in the usual manner. Then 9.9 g. (0.05 mole) of m-bromophenylisocyanate [made according to the method of K. Inukai and Y. Maki, *Kogyo Kagaku Zasshi*, 70 (4), 491–4 (1967)] dissolved in anhydrous benzene is added. The reaction mixture is stirred at room temperature for 1½ hours and the solvent then evaporated in vacuo to give a solid redisue of 1-(3-bromophenyl)-3-(1-methyl-2-pyrrolidylidene)urea. Recrystallizations from ethyl acetate yields the pure product, m.p. = 138°–149° C.

EXAMPLE XXXIX

1-Mesityl-3-(1-methyl-2-pyrrolidylidene)urea

The hydrochloride salt of 2-imino-1-methylpyrrolidine (6.73 g.; 0.05 mole) is converted to free base (4.0 g.; 0.05 mole) by adding 10 ml. of 50% NaOH to an aqueous slurry (minimal amount of water) of the salt and benzene extraction. After drying over K₂CO₃, the benzene solution is stirred at room temperature and 8.06 g. (0.05 mole) of 2,4,6-trimethylphenylisocyanate [made according to the method of K. Inukai and Y. Maki, *Kogyo Kagaku Zasshi*, 70 (4), 491–4 (1967)] dissolved in anhydrous benzene is added. The reaction mixture is stirred at room temperature for 1½ hours and then the solvent is evaporated in vacuo leaving an oily residue, which crystallizes on cooling. Recrystallization from acetone yields the pure product, 1-mesityl-3-(1-methyl-2-pyrrolidylidene)urea, m.p. = 121°–123° C.

EXAMPLE XL 1-m-Chlorophenyl-3-(1-ethyl-2-pyrrolidylidene)urea

The hydrochloride salt of 1-ethyl-2-iminopyrrolidine (7.43 g.; 0.05 mole) is converted to free base (5.6 g.; 0.05 mole) by adding 7 ml. of 50% NaOH to an aqueous slurry (minimal amount of water) of the salt and benzene extraction. After drying over K₂CO₃, the benzene solution is stirred at room temperature and 7.68 g. (0.05 mole) of m-chlorophenylisocyanate, dissolved in anhydrous benzene, is added. The reaction mixture is stirred for 1¾ hours and the solvent is then evaporated in vacuo leaving a solid residue, 1-m-chlorophenyl-3-(1-ethyl-2-pyrrolidylidene)urea. Recrystallizations from ethyl acetate yields the pure product, m.p. = 122°–124° C.

EXAMPLE XLI 1-m-Fluorophenyl-3-(1-methyl-2-pyrrolidylidene)urea hydrate

The hydrochloride salt of 2-imino-1-methylpyrrolidine is converted to free base (4.9 g.; 0.05 mole) in benzene in the usual manner. After drying over K₂CO₃, the benzene solution is stirred at room temperature and 6.86 g. (0.05 mole) of m-fluorophenylisocyanate, dissolved in anhydrous benzene, is added. Heat evolves and after 5–10 minutes, solid precipitates. Stirring is continued for one hour and the solid is then collected (m.p. = 142°–143° C.). Evaporation of solvent from the filtrate yields a second crop (m.p. = 142°–143° C.). Recrystallization of the combined solids from ethyl acetate gives the product, 1-m-fluorophenyl-3-pyrrolidylidene)urea hydrate, m.p. = 142°–143° C.

EXAMPLE XLII 1-(2,6-Dimethylphenyl)-3-(1-ethyl-2-pyrrolidylidene)urea

The hydrochloride of 1-ethyl-2-iminopyrrolidine (7.43 g.; 0.05 mole) is converted to free base (5.6 g.; 0.05 mole) in benzene in the usual manner. Then 7.35 g. (0.05 mole) of 2,6-dimethylphenylisocyanate, dissolved in anhydrous benzene, is added. The reaction mixture is stirred at room temperature for 1¾ hours and then the solvent is evaporated to dryness in vacuo to give an oily residue. Trituration with ethyl acetate and cooling produces a solid product, 1-(2,6-dimethylphenyl)-3-(1-ethyl-2-pyrrolidylidene)urea, m.p. = 120°–122° C. Recrystallization from acetone gives the pure product, m.p. - 121°–123° C.

EXAMPLE XLIII 1-(2,6-Dimethylphenyl)-3-(1,5-dimethyl-2-pyrrolidylidene)urea

The HBF₄ salt of 1,5-dimethyl-2-iminopyrrolidine (6.75 g.; 0.0337 mole) is converted to free base in benzene in the usual manner. Then 4.96 g. (0.0337 mole) of 2,6-dimethylphenylisocyanate, dissolved in anhydrous benzene, is added. The reaction mixture is stirred for 2 hours and then the solvent is evaporated in vacuo leaving an oily residue which eventually crystallizes. Recrystallization from ethyl acetate gives the product, 1-(2,6-dimethylphenyl)-3-(1,5-dimethyl-2-pyrrolidylidene)urea, m.p. 120°–122° C.

EXAMPLE XLIV 1-m-Chlorophenyl-3-(1,5-dimethyl-2-pyrrolidylidene)urea

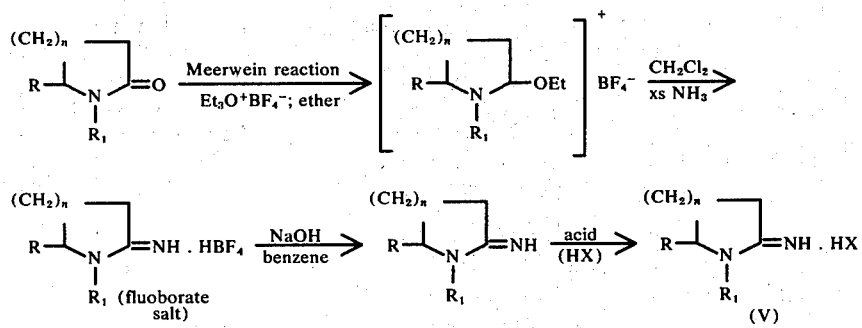

The HBF$_4$ salt of 1,5-dimethyl-2-iminopyrrolidine (6.75 g.; 0.0337 mole) is converted to free base in benzene in the usual manner. Then 5.16 g. (0.0337 mole) of m-chlorophenylisocyanate, dissolved in anhydrous benzene, is added. The reaction mixture is stirred for 2 hours and then the solvent is evaporated in vacuo leaving a solid residue of 1-m-chlorophenyl-3-(1,5-dimethyl-2-pyrrolidylidene)urea, m.p. = 129°–130° C. After recrystallization from ethyl acetate, the m.p. is still 129°–130° C.

EXAMPLE XLV

This example describes a general procedure for making the acid addition salts of formula (V). The fluoborate is initially prepared from which other acid addition salts are readily obtained.

Triethyloxinium fluoborate is prepared on a 0.6 mole scale from 113.55 g. (0.80 mole) of boron trifluoride etherate and 55.52 g. (0.60 mole) of epichlorohydrin in anhydrous ether according to the method of Meerwein et al., Ann. 641, 1 (1961). After the oily crystals have been washed with fresh anhydrous ether by decantation, 0.60 mole of the appropriate 2-pyrrolidone or 2-piperidone of the formula:

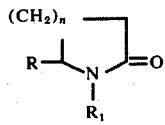

wherein n, R and R$_1$ are as previously defined, is added to an anhydrous methylene chloride solution of the oxonium salt. After stirring for periods of about 2 to 17 hours, depending upon the particular rate of reaction, anhydrous ammonia is bubbled into the reaction mixture at such a rate that reflux is obtained (due to the heat of reaction upon addition of the ammonia). After the initial reaction subsides, addition of further ammonia cools the reaction mixture which is then stirred at ambient temperatures until completion of the reaction. Subsequent removal of both excess ammonia and solvent in vacuo gives a residue of the respective 2-iminopyrrolidine or 2-iminopiperidine fluoborate salt which is then recovered and purified by conventional recrystallization techniques from appropriate solvents. The fluoborate salts are converted to the corresponding free base form by treatment with strong alkali, e.g. 10–50% NaOH, and extracted into organic solvents, e.g., ether, benzene, methylene chloride and the like, from which other mineral or organic acid salts are obtained by standard techniques.

In accordance with the foregoing procedure, the following are examples of typical salts of formula (V) that are obtained:

| n | R | R$_1$ | HX | m.p. (°C.) |
|---|---|---|---|---|
| 1 | H | Me | HBF$_4$ | 109–111 |
| 1 | H | Me | HCl | 186–189* |
| 1 | H | Et | HCl | 181–185 |
| 1 | H | n-Bu | | 110–114.5 |
| | | | HO$_3$SNH—⟨(S)⟩ | |
| 1 | H | Rz | HBF$_4$ | 112–114 |
| 1 | H | Bz | HCl | 203–204* |
| 1 | Me | Me | HBF$_4$ | 100–102 |
| 2 | H | Me | HCl | ** |

*described in R. Kwok et al., J. Org. Chem., 32, 738 (1967).
**described in J. Renault, Ann. Chim. (Paris) 10, 135 (1955).

EXAMPLE XLVI

The aniline-to-carbamoyl chloride procedure described in U.S. Pat. No. 2,449,440 may be employed to prepare the following respective N-loweralkyl-(substituted)phenylcarbamoyl chlorides of formula (IV) from the appropriately substituted aniline precursor:
N-ethyl-phenylcarbamoyl chloride;
N-methyl-(4-bromophenyl)carbamoyl chloride;
N-n-butyl-(2-chlorophenyl)carbamoyl chloride;
N-tert-butyl-(4-chlorophenyl)carbamoyl chloride;
N-ethyl-(2-chloro-4-nitrophenyl)cabamoyl chloride;
N-isopropyl-(4-chlorophenyl)carbamoyl chloride;
N-methyl-(2,5-dichlorophenyl)carbamoyl chloride;
N-ethyl-(2-ethylphenyl)carbamoyl chloride;
N-methyl-(2,5-dimethoxyphenyl)carbamoyl chloride;
N-methyl-(3-trifluoromethylphenyl)carbamoyl chloride; and
N-methyl-(3-methyl-4-ethylphenyl)carbamoyl chloride.

EXAMPLE XLVII

The procedure of Example XII is repeated except that an equivalent amount of each N-loweralkyl-(substituted)phenylcarbamoyl chloride obtained in Example XLVI is employed to yield the following respective products:
1-ethyl-3-(1-methyl-2-pyrrolidylidene)-1-phenylurea;

1-methyl-3-(1-methyl-2-pyrrolidylidene)-1-(4-bromophenyl)urea;

1-n-butyl-3-(1-methyl-2-pyrrolidylidene)-1-(2-chlorophenyl)urea 1-tert-butyl-3-(1-methyl-2-pyrrolidylidene)-1-(4-chlorophenyl)urea;

1-ethyl-3-(1-methyl-2-pyrrolidylidene)-1-(2-chloro-4-nitrophenyl)urea;

1-isopropyl-3-(1-methyl-2-pyrrolidylidene)-1-(4-chlorophenyl)urea;

1-methyl-31-methyl-2-pyrrolidylidene)-1-(2,5-dichlorophenyl)urea;

1-ethyl-3-(1-methyl-2-pyrrolidylidene)-1-(2-ethylphenyl)urea;

1-methyl-3-(1-methyl-2-pyrrolidylidene)-1-(2,5-dimethoxyphenyl)urea;

1-methyl-3-(1methyl-2-pyrrolidylidene)-1-(2-trifluoromethylphenyl)urea; and 1-methyl-3-(1-methyl-2-pyrrolidylidene)-1-(3-methyl-4-ethylphenyl)urea.

EXAMPLES XLVIII

The procedures of Examples XXIX through XXXIII demonstrate the facility of making the subject compounds of formula (I) wherein $R_1$ is benzyl. By following such procedures, except that an equivalent amount of an appropriate phenylisocyanate is reacted with the 1-benzyl-2-iminopyrrolidine, the following respective products are obtained:

1-(1-benzyl-2-pyrrolidylidene)-3-phenylurea;
1-(1-benzyl-2-pyrrolidylidene)-3-(3,4-dimethoxyphenyl)urea;
1-(1-benzyl-2-pyrrolidylidene)-3-(4-nitrophenyl)urea;
1-(1-benzyl-2-pyrrolidylidene)-3-(2,4,6-trichlorophenyl)urea;
1-(1-benzyl-2-pyrrolidylidene)-3-(4-benzyloxyphenyl)urea;
1-(1-benzyl-2-pyrrolidylidene)-3-(3-trifluoromethyl-4-chlorophenyl)urea; and
1-(1-benzyl-2-pyrrolidylidene)-3-(4-fluoro-3-nitrophenyl)urea.

EXAMPLE XLIX

1-Phenyl-3-(1-methyl-2-piperidylidene)urea

The hydrochloride salt of 2-imino-1-methylpiperidine (7.43 g.; 0.05 mole) is converted to free base by adding 5 mls. of 50% NaOH to an aqueous slurry (using a minimal amount of water) of the salt and then extracting with benzene. After drying over $K_2CO_3$, the benzene solution is stirred at room temperature and 5.96 g. (0.05 mole) of phenylisocyanate, dissolved in anhydrous benzene, is added dropwise. Cloudiness occurs and eventually solid precipitates from the solution. The reaction mixture is stirred at room temperature overnight (about 17 hours). The solid is collected, m.p. = 145°–158° C. The filtrate is taken to dryness in vacuo to give further solid material. Repeated recrystallizations of the combined solids from methanol yields the pure product, 1-phenyl-3-(1-methyl-2-piperidylidene)urea, m.p. = 160°–161° C.

EXAMPLE L

1-(1-Methyl-2-piperidylidene)-3-(4-trifluoromethylphenyl)urea

The hydrochloride salt of 2-imino-1-methylpiperidine (7.60 g.; 0.068 mole) is converted to free base by adding 7 ml. of NaOH (50%) to an aqueous slurry (using a minimal amount of water) of the salt and then extracting with benzene. After drying over $K_2CO_3$, the benzene solution is filtered through diatomaceous earth. A benzene solution of 12.73 g. (0.068 mole) of p-trifluoromethylphenylisocyanate [prepared according to Inukai and Maki, Kogyo Kagaku Zasshi, 67 (5) 807–9 (1964[ is added to the above solution slowly. After 4 hours of stirring at room temperature, the benzene is evaporated in vacuo to give a solid residue. Repeated recrystallizations of the solid from methanol yields the pure product, 1-(1-methyl-2-piperidylidene)-3-(4-trifluoromethylphenyl)urea, m.p. = 154-155° C.

EXAMPLE LI

1-(4-Chlorophenyl)-3-(1-methyl-2-piperidylidene)urea

The hydrochloride salt of 2-imino-1-methylpiperidine (7.43 g.; 0.05 mole) is converted to the free base in benzene in the usual manner. After drying over $K_2CO_3$ and filtering, a benzene solution of 0.05 mole of p-chlorophenylisocvanate is added dropwise with stirring. After addition is complete, further stirring is continued for about 6 hours at room temperature. The benzene is evaporated in vacuo and the solid residue is recrystallized from methanol to give the product, 1-(4-chlorophenyl)-3-(1-methyl-2-piperidylidene)urea.

EXAMPLE LII

1-(1-Methyl-2-piperidylidene-3-(4-nitrophenyl)urea

The hydrochloride salt of 2-imino-1-methylpiperidine (7.43 g.; 0.05 mole) is converted to the free base in benzene in the usual manner. After drying over $K_2CO_3$ and filtering, a benzene solution of 0.05 mole of p-nitrophenylisocyanate is added dropwise with stirring. After addition is complete, further stirring is continued for about 6 hours at room temperature. The benzene is evaporated in vacuo and the solid residue is recrystallized from methanol to give the product, 1-(1-methyl-2-piperidylidene)-3-(4-nitrophenyl)urea.

EXAMPLE LIII

1-(4-Benzyloxyphenyl)-3-(1-methyl-2-piperidylidene)urea

The hydrochloride salt of 2-imino-1-methylpiperidine (7.43 g.; 0.05 mole) is converted to the free base in benzene in the usual manner. After drying over $K_2CO_3$ and filtering, a benzene solution of 0.05 mole of p-benzyloxyphenylisocyanate is added dropwise with stirring. After addition is complete, further stirring is continued for about 6 hours at room temperature. The benzene is evaporated in vacuo and the solid residue is recrystallized from methanol to give the product 1-(4-benzyloxyphenyl)-3-(1-methyl-2-piperidylidene)urea.

EXAMPLE LIV

By following the procedures of Examples XLIX-LIII, except that an equivalent amount of an appropriate phenylisocyanate is used, the following respective piperidylidene ureas of formula (I) are obtained:

1-(2-chloro-6-methylphenyl)-3-(1-methyl-2-piperidylidene)urea;
1-(2,4,6-trichlorophenyl)-3-(1-methyl-2-piperidylidene)urea;
1-(2,6-di-bromophenyl)-3-(1-methyl-2piperidylidence)urea;

1-(4-methylthiophenyl)-3-(1-methyl-2-piperidylidene)urea;
1-(3-methoxyphenyl)-3-(1-methyl-2-piperidylidene)urea;
1-(2,6-dimethoxyphenyl)-3-(1-methyl-2-piperidylidene)urea;
1-(3,4,5-trimethoxyphenyl)-3-(1-methyl-2-piperidylidene)urea;
1-(2,6-dimethylphenyl)-3-(1-methyl-2-piperidylidene)urea;
1-(2,4,6-trimethylphenyl)-3-(1-methyl-2-piperidylidene)urea;
1-(3,5-ditrifluoromethylphenyl)-3-(1-methyl-2piperidylidene)urea;
1-(2-chloro-3-trifluoromethylphenyl)-3-(1-methyl-3-piperidylidene)urea; and
1-(4-fluoro-3-nitrophenyl)-3-(1-methyl-3-piperidylidene)urea.

EXAMPLE LV

1-Methyl-3-(1-methyl-2-piperidylidene)-1-phenylurea

The hydrochloride salt of 2-imino-1-methylpiperidine (14.8 g.; 0.1 mole) is converted to free base by adding 10 ml. of 50% NaOH and extracting into benzene. After drying over $K_2CO_3$, the benzene layer is stirred at room temperature and 8.84 g. (0.05 mole) of N-methyl-phenylcarbamoyl chloride (prepared according to the method of J. A. Aeschlimann, U.S. Pat. No. 2,449,440), dissolved in anhydrous benzene, is added dropwise to this solution. The mixture is stirred at room temperature overnight (about 17hours ) and then filtered. The filtrate is taken to dryness is vacuo and the residue is dissolved in and recrystallized from hexane to give the product 1-methyl-3-(1-methyl-2-piperidylidene)-1-phenylurea.

EXAMPLE LVI

The procedure of Example LV is repeated except that an equivalent amount of each N-loweralkyl-(substituted)-phenylcarbamoyl chloride obtained in Example XLVI is employed to yield the following respective products:
1-ethyl-3-(1-methyl-2-piperidylidene)-1-phenylurea;
1-methyl-3-(1-methyl-2-piperidylidene)-1-(4-bromophenyl)urea;
1-n-butyl-3-(1-methyl-2-piperidylidene)-1-(2-chlorophenyl)urea;
1-tert-butyl-3-(1-methyl-2-piperidylidene)-1-(4-chlorophenyl)urea;
1-ethyl-3-(1-methyl-2-piperidylidene)-1-(2-chloro-4-nitro- phenyl)urea; 1-isopropyl-3-(1-methyl-2-piperidylidene)-1-(4-chlorophenyl)urea;
1-methyl-3-(1-methyl-2-piperidylidene)-1-(2,5-dichlorophenyl)urea,
1-ethyl-3-(1-methyl-2-piperidylidene)-1-(2-ethylphenyl)urea;
1-methyl-3-(1-methyl-2-piperidylidene)-1-(2,5-dimethoxyphenyl)-urea;
1-methyl-3-(1-methyl-2-piperidylidene)-1-(2-trifluoromethylphenyl)- urea; and
1-methyl-3-(1-methyl-2-piperidylidene)1-1(3-methyl-4-ethylphenyl)urea.

EXAMPLE LVII

The procedure of Example XLIII is repeated except that an equivalent amount of an appropriate phenylisocyanate is used as one of the reactants to yield the following respective products:
1-(1,5-dimethyl-2-pyrrolidylidene)-3-phenylurea;
1-(1,5-dimethyl-2-pyrrolidylidene)-3-p-trifluoromethylphenylurea;
1-(1,5-dimethyl-2-pyrrolidylidene)-3-m-methoxyphenylurea;
1-(1,5-dimethyl-2-pyrrolidylidene)-3-(4-benzyloxyphenyl)urea;
1-(1,5-dimethyl-2-pyrrolidylidene)-3-p-methylthiophenyl)urea;
1-(1,5-dimethyl-2-pyrrolidylidene)-3-(2,4,6-tribromophenyl)urea;
1-(1,5-dimethyl-2-pyrrolidylidene)-3-nitrophenyl)urea;
1-(1,5-dimethyl-2-pyrrolidylidene)-3-(3,4,5-trimethoxyphenyl)urea;
1-(1,5-dimethyl-2-pyrrolidylidene)-3-(2-chloro-6-methylphenyl)urea;
1-(1,5-dimethyl-2-pyrrolidylidene)-3-(3-trifluoromethyl-4-chlorophenyl)urea; and
1-(1,5-dimethyl-2-pyrrolidylidene)-3-(4-fluoro-3-nitrophenyl)-urea.

EXAMPLE LVIII

1(1-Methyl-2-pyrrolidylidene)-3-o-tolyl urea

A 6.73 g. (0.05 mole) sample of 2-imino-1-methylpyrrolidine HCl is treated with 50 ml. of benzene and 2 ml. of water. With stirring, 10 ml. of 50% sodium hydroxide is added. After stirring about one minute, the benzene layer is decanted onto anhydrous $K_2CO_3$ and the extraction repeated twice with 50 ml. portions of benzene. The dried, combined extracts are filtered from the drying agent and the filtrate is treated with 6.66 g. (0.05 mole) of o-tolylisocyanate. After stirring overnight, the mixture is filtered from a small amount of insoluble material and the solvent removed in vacuo. Recrystallization from ethyl acetate and finally from ether gives the pure product, 1-(1-methyl-2-pyrrolidylidene)-3-o-tolyl urea, m.p. = 91°–93° C.

EXAMPLE LIX 1-(3,4-Dichlorophenyl)-3-(1-methyl-2-pyrrolidylidene)urea

A 6.73 g. (0.05 mole) sample of 2-imino-1-methylpyrrolidine HCl is converted to free base in the usual way. To the $K_2CO_3$-dried, benzene extracts are added a pre-filtered solution of 3,4-dichlorophenylisocyanate (9.4 g.; 0.05 mole). Almost immediately there is a separation of product. After stirring for a short time, the product is collected and recrystallized from acetone-methanol-water and finally from acetone-water to give the pure product, 1(3,4-dichlorophenyl)-3-(1-methyl-2-pyrrolidylidene)urea. m.p. = 160°–161° C.

EXAMPLE LX 1-(m-Cyanophenyl)-3-(1-methyl-2-pyrrolidinylidene)urea

A benzene solution of 2-imino-1-methylpyrrolidine (obtained from 11.33 g., 0.0843 mole, hydrochloride salt) is dried over potassium carbonate, filtered and to it added a toluene solution of m-cyanophenyl-isocyanate. After stirring the mixture for 1 hour, it is filtered and solvent removed in vacuo. The resulting solid is recrystallized from acetone to give the product, 1-(m- cyanophenyl)-3-(1-methyl-2-pyrrolidinylidene)urea, m.p. 145°–147° C.

EXAMPLE LXI 1-(4-Benzyloxy-3-chlorophenyl)-3-(1-methyl-2-pyrrolidinylidene)urea Ethyl 4-benzyloxy-3-chlorobenzoate [c.f., Jones & Robinson, J. Chem. Soc. 3845 (1955)] (32.0 g., 0.11 mole), 25 ml. methanol and 20 ml. 95% hydrazine are stirred under reflux for 8 hours and cooled to room temperature. The mixture is filtered and the resulting solid dried in vacuo to give 29.4 g. 4-benzyloxy-3-chlorobenzoic acid hydrazide (96.7% yield), m.p. 168°–171° C.

4-Benzyloxy-3-chlorobenzoic acid hydrazide (27.6 g., 0.1 mole) is suspended in 500 ml. 1N hydrochloric acid and the mixture cooled to about 0° C. A solution of sodium nitrite (7.0 g.) in 40 ml. water is added at such a rate as to keep the temperature below 5° C. The mixture is stirred at 5° C for ¾ hr., filtered and the precipitate dried in vacuo to give 27.8 g., (96.8% yield) 4-benzyloxy-3-chlorobenzoyl azide.

4-Benzyloxy-3-chlorobenzoyl azide (rigorously dried in vacuo at room temperature, 2.87 g., 0.01 mole) is heated to reflux in 25 ml. dry (molecular seive) toluene. After 1 hour, the mixture is homogeneous and the solution has a strong band in the infra red at 2300 cm$^{-1}$ due to 4-benzyloxy-3-chlorophenyl isocyanate, which tends to come out of solution on cooling. The toluene solution, warmed, may be used as such in the next step.

A benzene solution of 2-imino-1-methylpyrrolidine (obtained from 8.8 g., 0.055 mole, carbonate salt) is dried over potassium carbonate and filtered. The aforementioned warm toluene solution of 4-benzyloxy-3-chlorophenyl isocyanate is added by filtration. The mixture is stirred for ¼ hour, the solvent removed in vacuo and the residue crystallized by the addition of ether. Recrystallization from ethanol-ether affords a total of 12.6 g. (70.3% yield) 1-(4-benzyloxy-3-chlorophenyl)-3-(1-methyl-2-pyrrolidinylidene)urea, m.p. 115°–117° C.

EXAMPLE LXII 1-(m-Acetylphenyl)-3-(1-methyl-2-pyrrolidinylidene)urea 13.5 g. (0.1 mole) m-aminoacetophenone is dissolved in 50 ml dry monoglyme and the solution added to a saturated solution of phosgene in 100 ml dry monoglyme. The mixture is heated at reflux, and with continued passage of phosgene, for four hours. Monoglyme is removed in vacuo and the residue is dissolved in dry benzene, filtered through a filtering aid and the thus obtained benzene solution of m-acetylphenylisocyanate is used in the next step without further purification.

A solution of 2-imino-1-methylpyrrolidine (obtained from 10.09 g., 0.075 mole, hydrochloride salt) in benzene is dried over anhydrous potassium carbonate and filtered into a flask equipped with a thermometer. The aforementioned solution of m-acetylphenylisocyanate in benzene is filtered into the flask. The mixture exotherms from 24° to 43° C and is stirred to room temperature. The resultant precipitate is removed by filtration and recrystallized several times from acetone to afford the product, 1-(m-acetylphenyl)-3-(1-methyl)-2-pyrrolidinylidene)urea as an off-white solid, m.p. 154°–155.5° C.

EXAMPLE LXIII 1-(1-Methyl-2-pyrrolidinylidene)-3-(1-napthyl)urea

A solution of 2-imino-1-methylpyrrolidine (obtained from 6.91 g., 0.051 mole, hydrochloride salt) in benzene is dried over potassium carbonate and filtered. A solution of 1-naphthyl isocyanate (8.45 g., 0.05 mole) in benzene is added by filtration. The mixture is stirred for 1½ hr. at room temperature and the precipitate separated by filtration. Recrystallization from acetone affords the product, 1-(1-methyl-2-pyrrolidinylidene)-3-(1-naphthyl)urea, m.p. 148°–149° C.

EXAMPLE LXIV 1-(1-Methyl-2-pyrrolidinylidene)-3-[m-(methylthiophenyl)]urea m-Aminothioanisole (27.8 g., 0.2 mole) in 100 ml dry dimethoxyethane is added to a saturated solution of phosgene in 200 ml dry dimethoxyethane. Phosgene is passed into the refluxing mixture for a further 4 hr. and then the mixture is heated under nitrogen for 21 hours. Solvent is removed in vacuo to afford m-methylthiophenyl isocyanate as an amber oil which is dissolved in benzene for use in the next step.

A solution of 2-imino-1-methylpyrrolidine (obtained from 26.9 g., 0.2 mole, hydrochloride salt) in benzene is dried over anhydrous potassium carbonate and filtered into a flask equipped with a thermometer. A benzene solution of the previously prepared m-methylthiophenyl isocyanate is added by filtration and the mixture exotherms from 21° C to 42° C. After 1 hr. stirring, the mixture is filtered and solvent removed in vacuo. The residue is recrystallized from acetone to afford the product, 1-(1-methyl-2-pyrrolidinylindene)-3-[m-(methylthiophenyl)]urea, m.p. 110°–111° C. Recrystallizations from the same solvent raises the melting point to 116°–117° C.

EXAMPLE LXV

Hexahydro-2-imino-1-methyl-1H-azepine cyclohexanesulfamate

Epichlorohydrin (12.5 g., 0.14 m) is added rapidly to a stirred solution of boron trifluoride etherate (25.7 g., 0.18 m) in anhydrous ether (90 ml). After the initial vigorous exotherm, the mixture is refluxed for 3 hr. The ether is removed with a filter stick and the solid residue is washed twice with anhydrous ether. Dry methylene chloride (60 ml) is added to the triethyloxonium fluoroborate and hexahydro-1-methyl-1H-azepin-2-one (17 g., 0.13 m) in methylene chloride (20 ml) is added. The resulting solution is stirred overnight (about 15 hours) at room temperature. More methylene chloride is added and ammonia is bubbled into the solution. The mixture becomes exothermic and after ½ hr. it cools. After 3 hr., the ammonia addition is stopped, more methylene chloride is added and the mixture stirred overnight at room temperature. The inorganic material is filtered off and the filtrate evaporated to give 26 g. or residual oil which is washed with benzene to remove starting lactam. The benzene is decanted and the residual oil dried under vacuum to give 22.5 g. of fluoroborate salt as a waxy solid.

The fluoroborate salt is converted to the free base in benzene using 50% NaOH (7 ml). The benzene layer is decanted, filtered and dried ($K_2CO_3$). Evaporation gives 11.5 g. of oil which is dissolved in acetone (20 ml)

and treated with a solution of cyclohexanesulfamic acid (16.4 g) in warm acetone (150 ml). The resulting mixture is warmed briefly on a steam bath and then chilled and filtered to yield the product, hexahydro-2-imino-1-methyl-1H-azepine cyclohexanesulfamate, m.p. 142°–144° C. After recrystallization from ethanol-ether, the m.p. is 143°–145° C.

EXAMPLE LXVI

1-[2-(Hexahydro-1-methylazepinylindene)]-3-phenylurea

To a mixture of hexahydro-2-imino-1-methyl-1H-azepine cyclohexanesulfamate (1.25 g., 0.0041 mole) in benzene (20 ml) is added an excess of 50% sodium hydroxide. The mixture is swirled and the benzene layer decanted. The basic layer is washed with several more portions of benzene. The combined benzene extracts are dried ($K_2CO_3$) and evaporated to give 0.34 g (0.0027 m; 66%) of free base, which is dissolved in dry benzene (2 ml) and treated with phenylisocyanate (0.32 g, 0.0027 mole). After 15 min., the reaction solution is scratched slightly and a solid precipitates. The reaction mixture is then chilled and filtered to give the product, 1-[2-(hexahydro-1-methylazepinylidene)]-3-phenylurea, m.p. 135°–136° C. After recrystallized from ethyl acetate, the m.p. is 136°–137° C.

EXAMPLE LXVII 1-(Hexahydro-1-methyl-2-azepinylidene)-3-(2,6-xylyl)urea

To a mixture of hexahydro-2-imino-1-methyl-1H-azepine fluoroborate in dry benzene (75 ml) is added 50% sodium hydroxide (15 ml). The mixture is swirled and the benzene layer decanted. The basic layer is washed with two more portions of benzene (40 ml each). The combined benzene solutions are dried over potassium carbonate and filtered through supercel. The resulting filtrate is treated with a solution of 2,6-dimethylphenylisocyanate (11.45 g, 0.078 m) in dry benzene (10 ml). The reaction solution is stirred for ½ hr. and then evaporated almost to dryness. The residual liquid is triturated with warm anhydrous ether (100 ml). A solid forms and the mixture is chilled and filtered to give the product, 1-(hexahydro-1-methyl-2-azepinylidene)-3-(2,6-xylyl)urea, m.p. 128°–130° C. After recrystallization from acetone, the m.p. is 132°–133° C.

EXAMPLE LXVIII 1-m-Chlorophenyl-3-(hexahydro-1-methyl-2-azepinylidene)urea m-Chlorophenylisocyanate (9.4 g, 0.061 m) in a small volume of dry benzene is added to a benzene solution of hexahydro-2-imino-1-methyl-1H-azepine (obtained from the fluoroborate - 13.0 g, 0.061 m). The reaction solution is stirred for ½ hr. and then evaporated almost to dryness. The residual liquid is diluted with ether, and the ethereal solution is then evaporated almost to dryness and diluted with pentane. A gum forms; the mixture is scratched and chilled and the pentane decanted. After another wash with pentane, the gum is triturated with a small volume of warm ether. A solid forms and the mixture is chilled and filtered to give the product, 1-m-chlorophenyl-3-(hexahydro-1-methyl-2-azepinylidene)urea, 8.1 g, m.p. 115°–118° C. After recrystallization from a small volume of acetone, the m.p. is 119°–121° C.

EXAMPLE LXIX 1-(2,6-Dichlorophenyl)-3-(hexahydro-1-methyl-2-azepinylidene)urea A solution of 2,6-dichlorophenylisocyanate (12.0 g, 0.064 m) in warm dry benzene (30 ml) is filtered into a benzene solution of hexahydro-2-imino-1-methylazepine (obtained from the fluoroborate - 13.6 g, 0.064 m). The reaction solution is stirred for ½ hr. and then evaporated almost to dryness. The residual liquid is triturated with a small volume of warm anhydrous ether. A solid forms and the mixture is chilled and filtered, m.p. 133°–135° C. After recrystallization from isopropanol, the m.p. is 133°–138° C. A second recrystallization, this time from acetone, gives the product, 1-(2,6-dichlorophenyl)-3-(hexahydro-1-methyl-2-azepinylidene)urea, as a white crystalline solid, m.p. 143°–144° C.

EXAMPLE LXX

By following the procedures of Examples LXVI–LXIX, except that an equivalent quantity of an appropriate arylisocyanate is used to react with the hexahydro-2-imino-1-methyl-1H-azepine, the 1-aryl-3-hexahydroazepinylidene ureas of formula (I) can be prepared, for example:

1-(hexahydro-1-methyl-2-azepinylindene)-3-(3,4-dimethoxyphenyl)urea;
1-(hexahydro-1-methyl-2-azepinylidene)-3-(1-naphthyl)urea;
1-(5-chloro-2-methoxyphenyl)-3-(hexahydro-1-methyl-2-azepinylidene)urea;
1-(hexahydro-1-methyl-2-azepinylidene)-3-(p-nitrophenyl)urea;
1-(hexahydro-1-methyl-2-azepinylidene)-3-(p-tolyl)urea;
1-(hexahydro-1-methyl-2-azepinylidene)-3-(p-trifluoromethylphenyl)urea;
1-(4-benzyloxyphenyl)-3-(hexahydro-1-methyl-2-azepinylidene)urea;
1-(hexahydro-1-methyl-2-azepinylidene)-3-(p-methylthiophenyl)urea;
1-(2-chloro-5-trifluoromethylphenyl)-3-(hexahydro-1-methyl-2-azepinylidene)urea;
1-(2,4,6-tribromophenyl)-3-hexahydro-1-methyl-2-azepinylidene)urea;
1-(m-cyanophenyl)-3-(hexahydro-1-methyl-2-azepinylidene)urea; and
1-(m-acetylphenyl)-3-(hexahydro-1-methyl-2-azepinylidene)urea.

What is claimed is:

1. A process of alleviating anxiety which comprises systemically administering to an anxious individual a pharmaceutical composition in dosage unit form comprising per dosage from about 15 to about 350 mg of a member selected from the group consisting of a compound of the formula:

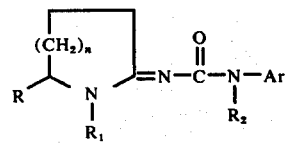

wherein n is the integer 1, 2 or 3, R is a member selected from the group consisting of hydrogen and loweralkyl, R₁ is a member selected from the group consisting of loweralkyl and benzyl, R₂ is a member selected from the group consisting of hydrogen and loweralkyl, and Ar is a member selected from the group consisting of phenyl, halophenyl, loweralkylphenyl, loweralkoxyphenyl, trifluoromethylphenyl, nitrophenyl, cyanophenyl, methylithiophenyl, loweralkylcarbonyl-phenyl and benzyloxyphenyl, provided that when said n is 2 or 3, then said R is hydrogen and said R₁ is loweralkyl, and the therapeutically active acid addition salts thereof in admixture with a pharmaceutical carrier.

2. A process of alleviating anxiety which comprises systemically administering to an anxious individual a pharmaceutical composition in dosage unit form comprising per dosage unit from about 15 to about 350 mg of a member selected from the group consisting of a compound of the formula:

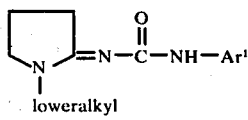

wherein Ar¹ is a member selected from the group consisting of halophenyl, loweralkylphenyl, nitrophenyl and trifluoromethylphenyl, and the therapeutically active acid addition salts thereof in admixture with a pharmaceutical carrier.

3. A process of alleviating anxiety which comprises systemically administering to an anxious individual a pharmaceutical composition in dosage unit form comprising per dosage unit from about 15 to about 350 mg of a member selected from the group consisting of 1-m-chlorophenyl-3-(1-methyl-2-pyrrolidylidene)urea and the therapeutically active acid addition salts thereof in admixture with a pharmaceutical carrier.

4. A process of alleviating anxiety which comprises systemically administering to an anxious individual a pharmaceutical composition in dosage unit form comprising per dosage unit from about 15 to about 350 mg of a member selected from the group consisting of 1-p-nitrophenyl-3-(1-methyl-2-pyrrolidylidene)urea and the therapeutically active acid addition salts thereof in admixture with a pharmaceutical carrier.

5. A pharmaceutical composition for alleviating anxiety in dosage unit form comprising per dosage unit from about 15 to about 350 mg of a member selected from the group consisting of 1-m-chlorophenyl-3-(1-methyl-2-pyrrolidylidene)urea and the therapeutically active acid addition salts thereof in admixture with a pharmaceutically acceptable carrier.

6. The composition of claim 5 wherein said dosage unit is a tablet.

7. The composition of claim 5 wherein said dosage unit is a capsule.

* * * * *

UNITED STATES PATENT AND TRADEMARK OFFICE
CERTIFICATE OF CORRECTION

PATENT NO. : 3,998,958
DATED : Dec. 21, 1976
INVENTOR(S) : Rasmussen, et al.

It is certified that error appears in the above-identified patent and that said Letters Patent are hereby corrected as shown below:

In Column 7, line 6, "madia" should read "media"
In Column 8, line 31, "required" should read "as required" in both columns
In Column 8, line 32, "ml" should read "1.0 ml" in both columns
In Column 10, line 40, "HCL" should read "HCl"
In Column 11, line 29, "(5 ) 807-809 (1964 )]," should read "(5) 807-809 (1964)],"
In Column 15, line 26, "hase" should read "base"
In Column 15, line 49, "1-(1-n-butyl2-" should read "1-(1-n-butyl-2-"
In Column 18, line 60, "REcrystallizations" should read "Recrystallizations"
In Column 22, line 32, in column $R_1$ "Rz" should read "Bz"
In Column 23, line 11, "1-methyl-31-methyl-" should read "1-methyl-3-(1-methyl"
In Column 24, line 8, "1964[" should read "1964]"
In Column 25, line 14, "2piperidylidene" should read "2-piperidylidene"

Signed and Sealed this

Twenty-seventh Day of June 1978

[SEAL]

Attest:

RUTH C. MASON
Attesting Officer

DONALD W. BANNER
Commissioner of Patents and Trademarks